(12) United States Patent
Gissman et al.

(10) Patent No.: US 6,953,579 B1
(45) Date of Patent: Oct. 11, 2005

(54) CHIMERIC VIRUS-LIKE PARTICLE OR CHIMERIC CAPSOMERS FROM BPV

(75) Inventors: Lutz Gissman, Wiesloch (DE); Martin Müller, Heidelberg (DE); Hermann Müller, Leipzig (DE)

(73) Assignee: Deutches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/913,204

(22) PCT Filed: Feb. 10, 2000

(86) PCT No.: PCT/DE00/00426

§ 371 (c)(1),
(2), (4) Date: Dec. 10, 2001

(87) PCT Pub. No.: WO00/47722

PCT Pub. Date: Aug. 17, 2000

(30) Foreign Application Priority Data

Feb. 11, 1999 (DE) .......................... 199 05 883

(51) Int. Cl.⁷ .......................... A61K 39/12; C12N 7/01; C12N 15/37; C07K 14/025
(52) U.S. Cl. ................ 424/192.1; 424/204.1; 435/235.1; 536/23.72; 536/23.4
(58) Field of Search .................... 435/235.1; 536/23.72, 536/23.4; 424/192.1, 204.1; 530/350

(56) References Cited

U.S. PATENT DOCUMENTS

| | | | | |
|---|---|---|---|---|
| 5,674,703 A | * | 10/1997 | Woo et al. .................. | 435/69.1 |
| 5,744,142 A | | 4/1998 | Lowy et al. .............. | 424/204.1 |
| 5,855,891 A | * | 1/1999 | Lowy et al. .............. | 424/192.1 |
| 6,380,157 B1 | * | 4/2002 | Jarrett et al. .................. | 514/12 |

FOREIGN PATENT DOCUMENTS

| | | |
|---|---|---|
| EP | 0133 123 A1 | 2/1985 |
| WO | WO 96/26277 | 8/1996 |
| WO | WO 99/02694 | 1/1999 |
| WO | WO 99/18220 | 4/1999 |

OTHER PUBLICATIONS

Goodrich et al. Veterinary Clinics of North America. Equine Practise. Dec. 1998, 14(3):607–23.*
Peng et al. Virology 240:147–157 (1998).*
Campo. Trends in Microbiology 3(3):92–97 (1995).*
Muller et al. Virology 234:93–111 (1997).*
Chen, et al., "The Primary structure and genetic organizationof the bovien papilomavirus type 1 genome", *Nature*, 299:529–534 (1882) XP–000915049.
Groff, et al., "E6 Protein Bovine papillomavirus type 2", *EMBL DATABASE*, (1989) XP–002156901.
Groff, et al., "Probable E7 Protein Bovine papillomavirus type 2", *EMBL DATABASE*, (1989) XP–002156902.
Müler, et al., "Chimeric papillomavirus–like particles", *Virology, US, Academic Press, Orlando*, 234:93–111 (1997).
Potter, et al., "Nucleotide sequence of bovine Papillomavirus Type–2 late region", *Journal of General Virology*, 66:187–193 (1985) XP–000923183.

* cited by examiner

Primary Examiner—Mary E. Mosher
(74) Attorney, Agent, or Firm—Howrey, Simon, Arnold & White, LLP

(57) ABSTRACT

The present invention relates to chimeric virus-like particles (cVLPs) or chimeric capsomers (cCs) from BPV, fusion proteins and DNAs coding for said proteins and to the use of cVLPs or cCs for the immunization of ungulates, especially horses.

13 Claims, 6 Drawing Sheets

Fig. 1 (a)

BPV1L1 (1-469)

```
MALWQQGQKLYLPPTPVSKVLCSETYVQRKSIFYHAETERLLTIGHPYYPVSIGAKTVPK
VSANQYRVFKIQLPDPNQFALPDRTVHNPSKERLVWAVIGVQVSRGQPLGGTVTGHPTFN
ALLDAENVNRKVTTQTTDDRKQTGLDAKQCQILLLGCTPAEGEYWTTARPCVTDRLENGA
CPPLELKNKHIIDGDMMEIGFGAANFKEINASKSDLPLDIQNEICLYPDYLKMAEDAAGN
SMFFFARKEQVYVRHIWTRGGSEKEAPTTIFYLKQNKGDATLKIPSVHFGSPSGSLVSTD
NQIFNRPYWLFRAQGMNNGIAWNNLLFLIVGDNTRGTNLTISVASDGTPLTEYDSSKFNV
YHRHMEEYKLAFILELCSVEITAQTVSHLQGLMPSVLEHWEIGVQPPTSSILEDTYRVIE
SPATKCAENVIPAKEDPYAGFKFWNIDLKEKLSLDLCQFPLGRRFLAQQ
```
469 DID——
(GAG)

```
ATGGCGTTGTGGCAACAAGGCCAGAAGCTGTATCTCCCTCCAACCCCTGTAAGCAAGGTG
CTTTGCAGTGAAACCTATGTGCAAAGAAAAGCATTTTTTATCATGCAGAAACGGAGCGC
CTGCTAACTATAGGACATCCATATTACCCAGTGTCTATCGGGGCCAAAACTGTTCCTAAG
GTCTCTGCAAATCAGTATAGGGTATTTAAAATACAACTACCTGATCCCAATCAATTTGCA
CTACCTGACAGGACTGTTCACAACCCAAGTAAAGAGCGGCTGGTGTGGGCAGTCATAGGT
GTGCAGGTGTCCAGAGGGCAGCCTCTTGGAGGTACTGTAACTGGGCACCCCACTTTTAAT
GCTTTGCTTGATGCAGAAAATGTGAATAGAAAAGTCACCACCCAAACAACAGATGACAGG
AAACAAACAGGCCTAGATGCTAAGCAACAACAGATTCTGTTGCTAGGCTGTACCCCTGCT
GAAGGGGAATATTGGACAACAGCCCGTCCATGTGTTACTGATCGTCTAGAAAATGGCGCC
TGCCCTCCTCTTGAATTAAAAAACAAGCACATAGAAGATGGGGATATGATGGAAATTGGG
TTTGGTGCAGCCAACTTCAAAGAAATTAATGCAAGTAAATCAGATCTACCTCTTGACATT
CAAAATGAGATCTGCTTGTACCCAGACTACCTCAAAATGGCTGAGGACGCTGCTGGTAAT
AGCATGTTCTTTTTTGCAAGGAAAGAACAGGTGTATGTTAGACACATCTGGACCAGAGGG
GGCTCGGAGAAAGAAGCCCCTACCACAGATTTTTATTTAAAGAATAATAAAGGGGATGCC
ACCCTTAAAATACCCAGTGTGCATTTTGGTAGTCCCAGTGGCTCACTAGTCTCAACTGAT
AATCAAATTTTTAATCGGCCCTACTGGCTATTCCGTGCCCAGGGCATGAACAATGGAATT
GCATGGAATAATTTATTGTTTTTAACAGTGGGGGACAATACACGTGGTACTAATCTTACC
ATAAGTGTAGCCTCAGATGGAACCCCACTAACAGAGTATGATAGCTCAAAATTCAATGTA
TACCATAGACATATGGAAGAATATAAGCTAGCCTTTATATTAGAGCTATGCTCTGTGGAA
ATCACAGCTCAAACTGTGTCACATCTGCAAGGACTTATGCCCTCTGTGCTTGAAAATTGG
GAAATAGGTGTGCAGCCTCCTACCTCATCGATATTAGAGGACACCTATCGCTATATAGAG
TCTCCTGCAACTAAATGTGCAAGCAATGTAATTCCTGCAAAAGAAGACCCTTATGCAGGG
TTTAAGTTTTGGAACATAGATCTTAAAGAAAAGCTTTCTTTGGACTTAGATCAATTTCCC
TTGGGAAGAAGATTTTTAGCACAGCAA
```
1407
TATCGATAT——
(GGGGCAGGA)

Fig. 1 (b)

BPV1E6

MDLKPFARTNPFSGLDCLWCREPLTEVDAFRCMVKDFHVVIREGCRYGACTICLENCLAT
ERRLWQGVPVTGEEAELLHGKTLDRLCIRCCYCGKLTKNEKHRHVLFNEFFCKTRANII
RGRCYDCCRHGSRSKYP

ATGGACCTGAAACCTTTTGCAAGAACCAATCCATTCTCAGGGTTGGATTGTCTGTGGTGC
AGAGAGCCTCTTACAGAAGTTGATGCTTTTAGGTGCATGGTCAAAGACTTTCATGTTGTA
ATTCGGGAAGGCTGTAGATATGGTGCATGTACCATTTGTCTTGAAAACTGTTTAGCTACT
GAAAGAAGACTTTGGCAAGGTGTTCCAGTAACAGGTGAGGAAGCTGAATTATTGCATGGC
AAAACACTTGATAGGCTTTGCATAAGATGCTGCTACTGTGGGGCAAACTAACAAAAAAT
GAAAAACATCGGCATGTGCTTTTTAATGAGCCTTTCTGCAAAACCAGAGCTAACATAATT
AGAGGACGCTGCTACGACTGCTGCAGACATGGTTCAAGGTCCAAATACCCATAG

BPV1E7

MVQGPNTHRNLDDSPAGPLLILSPCAGTPTRSPAAPDAPDFRLPCHFGRPTRKRGPTTPP
LSSPGKLCATGPRRVYSVTVCCGNCGKELTFAVKTSSTSLLGFEHLLNSDLDLLCPRCES
RERHGKR

ATGGTTCAAGGTCCAAATACCCATAGAAACTTGGATGATTCACCTGCAGGACCGTTGCTG
ATTTTAAGTCCATGTGCAGGCACACCTACCAGGTCTCCTGCAGCACCTGATGCACCTGAT
TTCAGACTTCCGTGCCATTTCGGCCGTCCTACTAGGAAGCGAGGTCCCACTACCCCTCCG
CTTTCCTCTCCCGGAAAACTGTGTGCAACAGGGCCACGTCGAGTGTATTCTGTGACTGTC
TGCTGTGGAAACTGCGGAAAAGAGCTGACTTTTGCTGTGAAGACCAGCTCGACGTCCCTG
CTTGGATTTGAACACCTTTTAAACTCAGATTTAGACCTCTTGTGTCCACGTTGTGAATCT
CGCGAGCGTCATGGCAAACGATAA

Fig. 1 (c)

BPV2E6

MDLQSFSRGNPFSGLACVWCREPLTEVIAFRCMIKDFHVVYRDGVKFGACTTCLENCLDK
ERRLWKGVPVTGEEAQLLHGKSLDRLCIRCCYCGGKLTKNEKQRHVLYNEPFCKTRSNII
RGRCYDCCRHGSRSNYP

ATGGACCTGCAAAGTTTTTCCAGAGGCAATCCTTTCTCAGGATTGGCCTGTGTTTGGTGC
AGGGAGCCTCTCACAGAAGTTGATGCTTTTAGGTGCATGATAAAAGACTTTCATGTTGTA
TACCGAGATGGTGTGAAATTTGGTGCATGTACCACTTGTCTTGAGAACTGCTTAGATAAA
GAAAGAAGACTGTGGAAAGGTGTGCCAGTAACAGGTGAGGAAGCTCAATTATTGCATGGC
AAATCCCTTGATAGGCTTTGCATAAGATGCTGCTACTGTGGGGAAAACTAACCAAAAAC
GAGAAGCAGCGGCATGTGCTTTATAATGAGCCTTTTTGCAAAACGAGATCTAACATAATA
AGAGGACGCTGCTACGACTGCTGCAGACATGGTTCAAGGTCCAACTACCCATAG

BPV2E7

MVQGPTTHRNLDDSPAGPLLILSPCAGTPTRVPAAPDAPDFRLPCHFGRPTRKRGPSTPP
LSSPGKVCATGPRRVYSVTVCCGHCGKDLTFAVKTGSTTLLGFEHLLNSDLDLLCPRCES
RERHGKR

ATGGTTCAAGGTCCAACTACCCATAGAAACTTGGATGATTCACCTGCAGGACCGTTGCTG
ATTTTAAGTCCATGTGCAGGCACACCTACCAGGGTTCCTGCAGCACCTGATGCACCCGAT
TTCAGACTTCCGTGCCATTTCGGCCGTCCTACTAGAAGCGAGGTCCCTCTACGCCTCCG
CTTTCCTCTCCCGGAAAAGTGTGTGCAACAGGCCCACGTCGAGTGTACTCTGTGACTGTC
TGCTGCGGACACTGCGGAAAGGACCTTACATTTGCTGTCAAGACTGGCTCTACGACCTTG
CTGGGCTTCGAACACCTATTAAACTCAGATTTGGACCTGTTGTGTCCCCGTTGCGAATCT
CGCGAGCGTCATGGCAAACGATAA

Fig. 2 (a)

BPV2L1 (1-469)

MALWCQGQKLYLPPTPVSKVLCSETYVQRKSIFYHAETERLLTVGHPYYQVTVGDKTVFK
VSANQFRVFKIQLPDPNQFALPDRTVHNPSKERLVWAVIGVQVSRGQPLGGTVTGHPTFN
ALLDAENVNRKVTAQTTDDRKQTGLDAKQQILLLGCTPAEGEYWTTAPPCVTDRLENGA
CPPLELKNKHIEDGDMMEIGFGAADFKTLNASKSDLPLDIQNEICLYPCYLKMAEDAAGN
SMFFTARKEQVYVRHIWTRGGSEKEAPSKDFYLKNGRGEETLKIPSVHFGSPSGSLVSTD
NQIFNRPYWLFPAQGMNNGIAWNNLLFLTVGDNTRGTNLSISVAADGNALSEYDTGKFNL
YHRHMEIYKLAFILELCSVEITAQTLSHLQGLMFSVLQNWEIGVQPPASSILEDTYRYIE
SPATKCASNVIPPKEDPYAGLKFWSIDLKEKLSLDLQFPLGRRFLACQ
                                             469
                                             DID ——
                                             (GAG)

ATGGCGTTGTGGCAACAAGGCCAAAAGCTGTATCTCCCTCCAACCCCTGTAAGCAAGGTG
CTATGCAGTGAAACCTATGTGCAAAGAAAAGCATATTCTATCATGCAGAAACGGAACGC
CTGTTAACTGTAGGACATCCATACTACCAAGTCACTGTGGGGACAAAACTGTTCCCAAA
GTGTCTGCTAATCAATTTAGAGTTTTTAAAATACAGCTCCCCGATCCCAATCAGTTTGCA
TTGCCTGATAGGACTGTGCACAATCCAAGCAAGGAGCGCCTGGTTTGGCTGTAATAGGG
GTTCAAGTATCTCGTGGCCAACCACTAGGAGGCACAGTTACTGGGCACCCCACTTTTAAT
GCTCTGCTTGATGCAGAAAATGTTAATAGAAAAGTTACTGCACAAACAACAGATGACAGG
AAGCAAACAGGATTAGATGCTAAGCAACAACAGATTCTGTTGCTGGGCTGTACCCCTGCA
GAAGGGGAATACTGGACCACAGCCCGTCCATGTGTTACTGATAGACTAGAAAATGGTGCG
TGTCCTCCTTTAGAATTAAAGAACAAACACATAGAAGATGGAGACATGATGGAAATAGGG
TTTGGTGCTGCTGACTTTAAAACACTAAATGCCAGTAAATCAGATCTACCTCTTGACATT
CAAAATGAAATATGCCTGTATCCAGACTACCTCAAAATGGCTGAAGATGCTGCTGGAAAC
AGTATGTTCTTCTTTGCAAGAAAAGAACAAGTGTATGTAAGGCATATATGGACTCGGGGG
GGCTCTGAAAAAGAAGCACCCAGTAAAGACTTCTACCTCAAAAATGGTAGAGGTGAAGAA
ACTCTAAAAATACCTAGTGTGCACTTTGGCAGTCCAGTGGATCCTTGGTGTCCACTGAT
AATCAAATATTTAACAGGCCTTATTGGCTATTCAGGGCTCAGGGCATGAACAATGGGATT
GCATGGAATAATTTATTATTTTTAACTGTAGGGGATAACACACGGGAACTAACCTTAGT
ATTAGTGTAGCTGCAGATGGAAACGCATTGTCAGAGTATGATACTGGCAAATTTAACCTA
TACCATAGGCATATGGAAGAATATAAGCTAGCATTTATATTGGAGCTGTGCTCTGTTGAG
ATTACTGCACAAACACTGTCACATCTGCAAGGACTGATGCCCTCTGTGCTACAAAACTGG
GAAATCGGGGTGCAACCTCCTGCTTCTTCTATTTTAGAAGATACTTATAGGTACATAGAG
TCTCCTGCAACTAAATGTGCAAGTAATGTTATACCACCCAAAGAAGACCCTTATGCAGGG
CTTAAGTTTTGGAGCATAGACTTAAAAGAAAAGCTGTCTTTGGACTTAGACCAATTTCCC
TTGGGAAGAAGATTCTTAGCTCAGCAA
                        1407
                          TATCGATAT ——
                          (GGGGCAGGA)

Fig. 2 (b)

BPV1E6

MDLKPFARTNPFSGLDCLWCREPLTEVDAFRCMVKDFHVVIREGCRYGACTICLENCLAT
ERPLWQGVPVTGEEAELLHGKTLDRICIRCCVCGGKLTKIEKHRHVLFNEPFCKTPANII
RGRCYDCCRHGSRSKYP

ATGGACCTGAAACCTTTTGCAAGAACCAATCCATTCTCAGGGTTGGATTGTCTGTGGTGC
AGAGAGCCTCTTACAGAAGTTGATGCTTTTAGGTGCATGGTCAAAGACTTTCATGTTGTA
ATTCGGGAAGGCTGTAGATATGGTGCATGTACCATTTGTCTTGAAAACTGTTTAGCTACT
GAAAGAGACTTTGGCAAGGTGTTCCAGTAACAGGTGAGGAAGCTGAATTATTGCATGGC
AAAACACTTGATAGGCTTTGCATAAGATGCTGCTACTGTGGGGCAAACTAACAAAAAT
GAAAAACATCGGCATGTGCTTTTTAATGAGCCTTTCTGCAAAACCAGAGCTAACATAATT
AGAGGACGCTGCTACGACTGCTGCAGACATGGTTCAAGGTCCAAATACCCATAG

BPV1E7

MVQGPNTHRNLDDSPAGPLLILSPCAGTPTRSPAAPDAPDFRLPCHFGRPTRKRGPTTPP
LSSPGKLCATGPRRVYSVTVCCGNCGKELTFAVKTSSTSLLGFEHLLNSDLDLLCPRCES
RERHGKR

ATGGTTCAAGGTCCAAATACCCATAGAAACTTGGATGATTCACCTGCAGGACCGTTGCTG
ATTTTAAGTCCATGTGCAGGCACACCTACCAGGTCTCCTGCAGCACCTGATGCACCTGAT
TTCAGACTTCCGTGCCATTTCGGCCGTCCTACTAGGAAGCGAGGTCCCACTACCCCTCCG
CTTTCCTCTCCCGGAAAACTGTGTGCAACAGGGCCACGTCGAGTGTATTCTGTGACTGTC
TGCTGTGGAAACTGCGGAAAAGAGCTGACTTTTGCTGTGAAGACCAGCTCGACGTCCCTG
CTTGGATTTGAACACCTTTTAAACTCAGATTTAGACCTCTTGTGTCCACGTTGTGAATCT
CGCGAGCGTCATGGCAAACGATAA

Fig.2 (c)

BPV2E6

MDLQSFSRGNPFSGLACVWCREPLTEVIAFRCMIKDFEVIYRDGVKFGACTTCLENCLCK
ERRLWKGVPVTGEEAQLLHGKSLDRLCIRCCVCGGKLTKMEKQRHVLYNEPFCKTRSNII
RGRCYDCCRHGSRSNYP

ATGGACCTGCAAAGTTTTTCCAGAGGCAATCCTTTCTCAGGATTGGCCTGTGTTTGGTGC
AGGGAGCCTCTCACAGAAGTTGATGCTTTTAGGTGCATGATAAAAGACTTTCATGTTGTA
TACCGAGATGGTGTGAAATTTGGTGCATGTACCACTTGTCTTGAGAACTGCTTAGATAAA
GAAAGAAGACTGTGGAAGGTGTGCCAGTAACAGGTGAGGAAGCTCAATTATTGCATGGC
AAATCCCTTGATAGGCTTTGCATAAGATGCTGCTACTGTGGGGAAACTAACCAAAAAC
GAGAAGCAGCGGCATGTGCTTTATAATGAGCCTTTTTGCAAAACGAGATCTAACATAATA
AGAGGACGCTGCTACGACTGCTGCAGACATGGTTCAAGGTCCAACTACCCATAG

BPV2E7

MVQGPTTHRNLDDSFAGPLLILSPCAGTPTRVPAAPDAPDFRLPCHFGRPTRKRGPSTPP
LSSPGKVCATGPRRVYSVTVCCGHCGADLTFAVKTGSTTLLGFEHLLNSDLDLLCPRCES
RERHGKR

ATGGTTCAAGGTCCAACTACCCATAGAAACTTGGATGATTCACCTGCAGGACCGTTGCTG
ATTTTAAGTCCATGTGCAGGGACACCTACCAGGGTTCCTGCAGCACCTGATGCACCCGAT
TTCAGACTTCCGTGCCATTTCGGCCGTCCTACTAGGAAGCGAGGTCCCTCTACGCCTCCG
CTTTCCTCTCCCGGAAAAGTGTGTGCAACAGGGCCACGTCCAGTGTACTCTGTGACTGTC
TGCTGCGGACACTGCGGAAAGGACCTTACATTTGCTGTCAAGACTGGCTCTACGACCTTG
CTGGGCTTCGAACACCTATTAAACTCAGATTTGGACCTGTTGTGTCCCCGTTGCGAATCT
CGCGAGCGTCATGGCAAACGATAA

CHIMERIC VIRUS-LIKE PARTICLE OR CHIMERIC CAPSOMERS FROM BPV

This application is a National Stage of International Application PCT/DE00/00426, filed Feb. 10, 2000; which claims the priority of DE 199 05 88.30, filed Feb. 11, 1999.

The present invention relates to chimeric virus-like particles (cVLPs) or chimeric capsomers (cCs) from BPV, fusion proteins and DNAs coding for said proteins as well as the use of the cVLPs or the cCs for the immunization of ungulates, especially horses.

Sarcoids frequenztly occur in ungulates, in particular horses. They are exophytically growing skin tumors which may be localized on various parts of the body. Sarcoids often have sequences of bovine papilloma viruses (BPVs). Sarcoids are usually removed by means of an operation, which due to their localization, e.g. at the eye or ear, is often difficult. Sarcoids also have a high recurrence rate, thus representing a considerable problem for veterinary surgeons, breeders and owners.

It is thus the object of the present invention to provide a product serving for taking steps against sarcoids, the above drawbacks being avoided.

According to the invention this is achieved by the subject matters defined in the claims.

The present invention is based on Applicant's insights that cVLPs or cCs from BPV, the latter being incomplete cVLPs, are suitable for taking prophylactic and therapeutic steps against sarcoids of ungulates, in particular horses. Such cVLPs or cCs contain fusion proteins which comprise fragments of L1 or L2 proteins from BPV and early proteins from BPV, e.g. E6 or E7 proteins, or fragments thereof. He realized that antibodies can be induced by the cVLPs or cCs or cytotoxic T cells can be stimulated which are directed against BPV. He also realized that an infection caused by BPV can be prevented by the antibodies and a rejection of the sarcoids and the BPV-infected cells can be achieved by the cytotoxic T cells.

According to the invention Applicant's insights are utilized to use cVLPs or cCs from BPV for immunizing undulates against sarcoids, the cVLPs or cCs containing fusion proteins comprising fragments of L1 or L2 proteins from BPV and early proteins from BPV, e.g. E6 or E7 proteins, or fragments thereof.

The term "BPV" comprises any types of BPV, in particular the types BPV1 and BPV2.

The term "fragments of L1 or L2 proteins from BPV" comprises any fragments of these proteins which may fold or collect to form cVLPs or cCs. It may be favorable for the fragments to also be able to induce the formation of antibodies directed against BPV. Preferred fragments are those comprising amino acid sequences 1–469 or 1–472 of the L1 protein. The fragments may also differ from the corresponding wild-type fragments by one or more amino acids. This may show in terms of additions, deletions, substitutions and/or inversions of individual amino acids. In particular, the fragments may include amino acids which support the formation of cVLPs or cCs or the induction of antibodies directed against BFV.

The expression "fragments of E6 or E7 proteins from BPV" comprises any fragments of these proteins which contain epitopes for cytotoxic T cells and can be folded or collected by fusion with the above fragments of the L1 or L2 proteins to form cVLPs or cCs. Preferably the fragments do not have more than 55 amino acids. It is especially preferred for the fragments of E6 proteins from BPV1 or BPV2 to include amino acid sequences 1–55, 47–101 or 83–137. Fragments of E7 proteins from BPV1 or BPV2 preferably include the amino acid sequences 1–54, 46–100 or 72–127. The fragments may also differ from the corresponding wild-type fragments by one or more amino acids. This may show in terms of additions, deletions, substitutions and/or inversions of individual amino acids. In particular, the fragments may include amino acids which support the formation of cVLPs or cCs or the stimulation of cytotoxic T cells directed against. BPV.

The term "cVLPs or cCs from BPV" comprises any cVLPs or cCs containing fusion proteins which comprise the above fragments of L1 or L2 proteins from BPV and early proteins from BPV, e.g. E6 or E7 proteins, or the above fragments thereof. cVLPs or cCs may be provided by common methods. For example, the DNAs coding for the individual fragments or proteins may be linked to one another in a ligase reaction. The resulting DNA molecules can be expressed in cells, e.g. *E. coli,* yeast, mammalian or insect cells so as to obtain fusion proteins which can fold or collect to form cVLPs or cCs. It may be favorable to express the DNA molecules coding for the fusion proteins in the presence of virus DNA, e.g. vacciniavirus or baculovirus DNA, the expression with the baculovirus DNA being preferred. Reference is made to the below examples. Resulting cVLPs or cCs may contain one or more types of fusion proteins, wherein the fusion proteins of several types can differ as regards the fragments of the L1 or L2 proteins and the early proteins or the fragments thereof. The cVLPs or cCs may be isolated by common methods, e.g. density gradient centrifugation.

The expression "ungulates" comprises any kind of hoofed animals, in particular horses, cattle and game.

The term "immunization of ungulates against sarcoids" comprises any methods by means of which it is possible to induce antibodies in ungulates by the above cVLPs or cCs or stimulate cytotoxic T cells directed against BPV. It may be favorable to inject about 100 µg–1 mg of the cVLPs or cCs per animal. It may also be favorable to carry out a booster injection with about the same amount after about 14 days. In this case, it may be particularly favorable to use L1 or L2 fragments of different BPV types for the individual injections. Antibodies directed against BPV or cytotoxic T cells can be detected by common methods. For example, reference is made to Roden et al., Journal of Virology, (November 1994), 7570–7574, or Brostrom et al., Am. J. Vet. Res. 7, (July 1996), 992–999.

Another subject matter of the present invention is a cVLP or cC from BPV, which contains a fusion protein comprising the amino acid sequence of FIG. 1 or FIG. 2 or an amino acid sequence differing therefrom by one or more amino acids.

The expression "an amino acid sequence differing by one or more amino acids" indicates that the partial sequences of its individual fragments differ from the corresponding partial sequences of the fusion protein of FIG. 1 or FIG. 2. The differences may show in terms of additions, deletions, substitutions and/or inversions of individual amino acids.

Reference is also made to the above statements on the individual fragments.

Another subject matter of the present invention is a fusion protein contained in the above cVLP or cC. The above explanations apply correspondingly to this fusion protein.

Another subject matter of the present invention is a nucleic acid coding for an above fusion protein. The nucleic acid may be an RNA or a DNA. A DNA is preferred which comprises the following:

(a) the DNA of FIG. 1 or FIG. 2 or a DNA differing therefrom by one or more base pairs, or (b) a DNA related to the DNA from (a) via the degenerated genetic code.

The expression "a DNA differing by one or more base pairs" indicates that its partial sequences coding for the individual fragments differ from the corresponding partial sequences of the DNA coding for the fusion protein of FIG. 1 or FIG. 2. The differences may show in terms of additions, deletions, substitutions and/or inversions of individual base pairs. Reference is also made to the above explanations on the individual fragments. A preferred DNA of FIG. 1, which codes for BPVL1 (1–469) and BPVE7$_{1-127}$ or BPVE7$_{1-54}$, was deposited as pVL1393-BPV1L1/E7$_{1-127}$ or pVL1393-BPV1L1/E7$_{1-54}$ with the DSMZ (Deutsche Sammlung von Mikroorganismen und Zellkulturen [German-type collection of microorganisms and cell cultures]) under DSM 12628 or 12627 on Jan. 14, 1999.

A DNA according to the invention may be present as such or in combination with any other DNA. In particular, a DNA according to the invention may be present in an expression vector. A person skilled in the art is familiar with examples thereof. In the case of an expression vector for *E. coli*, these are e.g. pGEMEX, pUC derivatives, pGEX-2T, pET3b and pQE-8. For the expression in yeast, e.g. pY100 and Ycpad1 have to be mentioned while e.g. pKCR, pEFBOS, cDM8 and pCEV4 have to be indicated for the expression in mammalian cells. The bacculovirus expression vector pAcSGHisNT-A and pVL 1393 are especially suitable for the expression in insect cells.

The person skilled in the art is familiar with suitable cells to express the DNA according to the invention, which is present in an expression vector. Examples of such cells comprise the *E. coli* strains HB101, DH1, x1776, JM101, JM 109, BL21, SG 13009, and DH5$_\alpha$, the yeast strain *Saccharomyces cerevisiae* and the mammalian cells L, NIH, 3T3, FM3A, CHO, COS, Vero and HeLa as well as the insect cells sf9.

In addition, the person skilled in the art knows conditions of culturing transformed or transfected cells. He is also familiar with methods of isolating and purifying the fusion protein expressed by the DNA according to the invention. He also knows methods of isolating and purifying the VLPs obtained by folding or collecting the fusion protein.

Another subject matter of the present invention is a kit. Such a kit comprises one or more of the following components:

(a) a cVLP or cC according to the invention,
(b) a fusion protein according to the invention,
(c) a DNA according to the invention, and
(d) common auxiliary agents, such as carriers, buffers, solvents, controls, etc.

One or more representatives of the individual components may be present each. Regarding the individual terms, reference is made to the above explanations. They apply here analogously.

By means of the present invention it is possible to immunize ungulates, in particular horses, against sarcoids. The immunization comprises both the induction of antibodies and the stimulation of cytotoxic T cells which are directed against BPV. It is thus possible to take prophylactic and therapeutic steps against sarcoids of ungulates, in particular horses.

BRIEF DESCRIPTION OF THE FIGURES

FIG. 1 shows the amino acid and DNA sequences of fusion proteins according to the invention which comprise a fragment of the L1 proteins from BPV1, namely 1–469 or 1–472, and BPV1/2 E6 or E7 proteins or fragments thereof. The L1 fragment from BPVI (1–469) has the additional amino acids DID at the C terminus (470472; TATCGATAT). They do not originate from the L1 protein but from the restriction site EcoRV/ClaI inserted in the DNA. The L1 fragment from BPV1 (1–472) has the natural amino acids GAG at the C terminus (470–472; GGGGCAGGA). The E6 fragments from PBV1/2 comprise the amino acid sequences 1–55, 47–101 or 83–137. The E7 fragments from BPV1/2 comprise the amino acid sequences 1–54, 46–100 or 72–127. The fusion proteins may be present in cVLPs or cCs according to the invention (SEQ ID NOs: 1–10)

FIG. 2 shows the amino acid and DNA sequences of fusion proteins according to the invention, which comprise a fragment of the L1 protein from BPV2, namely 1–469 or 1–472, and BPV1/2 E6 or E7 proteins or fragments thereof. The L1 fragment from BPV2 (1–469) has the additional amino acids DID at the C terminus (470–472; TATCGATAT). They do not originate from the L1 protein but from the restriction site EcoRV/ClaI inserted in the DNA. The L1 fragment from BPV2 (1–472) has the natural amino acids GAG at the C terminus (470–472; GGGGCAGGA). The E6 fragments from BPV1/2 comprise the amino acid sequences 1–55, 47–101 or 83–137. The E7 fragments from BPV1/2 comprise the amino acid sequences 1–54, 46–100 or 72–127. The fusion proteins may be present in cVLPs or cCs according to the invention (SEQ ID NOs: 11–20).

The invention is explained by the below examples.

EXAMPLE 1

Production of cVLPs or cCs According to the Invention (A) Production of the 1–469 Fragment of the L1 Protein from BPV1

An expression plasmid coding for the L1 protein from BPV1, pUC19-BPV1-L1, is used as a basis. It is inserted in a PCR reaction in which the following primers 1 and 2 are used whose 5' ends on the L1 gene from BPV1 are opposite each other. Both primers carry a short spacer sequence (AAA) and an EcoRV cleavage site (underlined) at the 51 end. Primer 2 additionally contains a stop codon (TGA); The L1-specific sequences are printed in boldface.

```
                    7015                         6986
Primer 1. AAAGATATCTTGCTGTGCTAAAAATCTTCTTCCCAAGGG (SEQ ID NO:21)

7038                         7066
Primer 2. AAAGATATCTGAGAAAACGAAGAATTAGCCAAAAAACTTCC (SEQ ID NO:22)
```

Resulting PCR products are purified, cleaved using EcoRV and circularized with T4 ligase before they are used for transforming E. coli DH5$_\alpha$ cells. Clones are obtained which are tested for the presence of an EcORV cleavage site which is not present in either the L1 gene or the vector. Following sequencing, it shows that one of these clones codes for the 1–469 fragment of the L1 protein from BPV1. This clone is referred to as pUC BPV1-L1$_A$AC.

(B) Production of Fragments of the E7 Protein from BPV1

An expression plasmid coding for the E7 protein from BPV1, pUC19-BPVI-E7, is used as a basis. It is inserted in a PCR reaction which uses the following primers 3, 4 and 5. Primers 3 to 5 contain a spacer (TTTT) and an EcoRV cleavage site (underlined) at the 5' end. Primer 3 additionally contains the sequence GAT (underlined, in italics) so as to generate a ClaI cleavage site (ATC GAT) overlapping with the EcoRV cleavage site (to identify the insert in sense orientation) and to insert an additional Asp. Primer 5 additionally contains a stop codon. The E7-specific sequences are printed in boldface. Primers 3 and 4 are used to amplify the complete gene of the E7 protein while primers 3 and 5 are used for the amplification of the 1–54 fragment of the E7 protein.

obtained and sequenced. It shows that two of these clones code for a fusion protein which comprises fragment 1–469 of the L1 protein and the E7 protein or the fragment 1–54 of the E7 protein. The first clone is referred to as pUCBPV1L1$_A$CBPVE7$_{1-127}$ and the second one is designated pUCBPV1L1$_A$CBPVE7$_{1-54}$.

(D) Production of cVLPs or cCs According to the Invention

The BPV sequences of pUCBPV1L1$_A$CBPVE7 or pUCBPV1L1$_A$CBPVE7$_{1-54}$ are cleaved from the vector using Bam HI and inserted in the Bam HI cleavage site of the transfer vector pVL 1393 (Invitrogen company). Clones are obtained after transforming E. coli DH5$_\alpha$ cells. Two of these clones have the above BPV sequences, one clone being referred to as pVLBPV1L1$_A$CBPVE7 and the other clone being designated pVLBPV1L1$_A$CBPVE7$_{1-54}$. The clones are co-transfected together with linearized baculovirus DNA (Baculo-Gold, Pharmingen) in SF9 cells by means of the calcium phosphate precipitation method. cVLPs or cCs according to the invention are obtained which are purified according to the method of Muller et al., Virology 234, 93–111. They contain the fusion proteins BPV1L1$_A$CBPVE7$_{1-127}$ or BPVL1$_A$CBPVE7$_{1-54}$.

```
                474 start                                  508
Primer 3: TTTTGATATCGATATGGTTCAAGTCCAAATACCCATAGAAAC (SEQ ID NO:23)

862                                833
Primer 4: TTTTGATATCTTATCGTTTGCCATGACGCTCGCGAGATTC (SEQ ID NO:24)

Stop 640
610
Primer 5: TTTGATATCTTATCGCTTCCTAGTAGGACGGCCGAAATGGCAC (SEQ ID NO:25)
```

Resulting PCR products are purified, cleaved using EcoRV and inserted in the expression vector bluescript via the EcoRV cleavage site. Having transformed E. coli DH5$_\alpha$ cells, clones are obtained which are tested for the presence of two EcORV sites, none of which is present in the E7 gene and only one of which is present in the vector. Following sequencing, it shows that two of these clones code for the complete E7 protein or for the 1–54 fragment of the E7 protein. The first clone is referred to as bluescript BPV1-E7 and the second clone is designated bluescript BPVI-E7$_{1-54}$.

(C) Production of Fusion Proteins According to the Invention

After cleavage with EcoRV, the E7 sequences are isolated from the bluescript BPV1-E7 and bluescript BPV1-E7$_{1-54}$ clones obtained in (B) by means of agarose gel electrophoresis and inserted in the EcoRV cleavage site of pUCBPV1-L1$_A$AC of (A). After transforming E. coli DH5$_\alpha$, clones are

EXAMPLE 2
Immunization of Horses Against Sarcoids

Two healthy horses and two horses operated on sarcoids are used. They are given by injection 100 µg–1 mg of the cVLPs or cCs of (D) +/− adjuvant. A booster injection with the same amount of VLPs is made after 14 days. Blood is withdrawn from the horses at different times and tested for induction of antibodies or stimulation of cytotoxic T cells directed against BPV. For this purpose, the methods described in Roden et al., Journal of Virology, (November 1994), 7570–7574 or Brostrom et al., Am. J. Vet. Res. 7, (July 1996), 992–999, are carried out.

It shows that both antibody induction and stimulation of cytotoxic T cells directed against BPV have occurred in the healthy horses. It also shows that the formation of relapses has been prevented in the horses operated on sarcoids as compared to the controls treated with placebos.

What is claimed is:

1. Chimeric virus-like particles (cVLPs) or chimeric capsomers (cCs) from BPV, which contain a fusion protein consisting of the amino acid sequences 1–469 or 1–472 of SEQ ID NO: 1 or 11, and the amino acid sequences 1–55, 47–101 or 83–137 of SEQ ID NO: 3 or 17 or the amino acid sequences 1–54, 46–100 or 72–127 of SEQ ID NO: 5 or 9.

2. A fusion protein of BPVL1 and the E6 or E7 protein from BPV1 or BPV2 consisting of:

the amino acid sequences 1469 or 1–472 of SEQ ID NOS: 1 or 11, and an amino acid chosen from the group consisting of the amino acid sequences 1–55, 47–101 or 83–137 of SEQ ID NOS: 3 or 17 or the amino acid sequences 1–54, 46–100 or 72–127 of SEQ ID NOS: 5 or 9.

3. A DNA coding for the fusion protein according to claim 2, wherein the DNA comprises a combination of SEQ ID NOS: 2 or 12 and SEQ ID NOS: 4, 6, 8 or 12, or a degenerate sequence thereof.

4. An expression vector containing the DNA according to claim 3.

5. A method of immunizing ungulates against sarcoids comprising the step of injecting cVLPS or cCs from BPV to the ungulates, wherein the VLPs or cCs contain a fusion protein which comprises a fragment of the L1 or L2 protein from BPV and an early protein from BPV.

6. The method of claim 5, wherein the fragment of the L1 protein comprises the amino acid sequences 1–469 or 1–472.

7. The method of claim 5 or 6, wherein the early protein is an E6 or E7 protein.

8. The method of claim 7, wherein the fragment of the E6 protein comprises the amino acid sequences 1–55, 47–101 and/or 83–137.

9. The method of claim 7, wherein the fragment of the E7 protein comprises the amino acid sequences 1–54, 46–100 and/or 72–127.

10. The method of claim 5 or 6, wherein the BPV is the BPV1 type or BPV2 type.

11. The method of claim 5 or 6, wherein the immunization results in a prophylaxis effect and/or treatment of sarcoids.

12. The method of claim 5 or 6, wherein the ungulates are horses.

13. The method of claim 5 or 6, wherein the fusion protein comprises the amino acid sequences 1–469 or 1–472 of SEQ ID NO: 1 or 11 and the amino acid sequences 1–55, 47–101 or 83–137 of SEQ ID NO: 3 or 17 or the amino acid sequences 1–54, 46–100 or 72–127 of SEQ ID NO: 5 or 9.

* * * * *

SEQUENCE LISTING

<160> NUMBER OF SEQ ID NOS: 25

<210> SEQ ID NO 1
<211> LENGTH: 472
<212> TYPE: PRT
<213> ORGANISM: Bovine papilloma virus

<400> SEQUENCE: 1

```
Met Ala Leu Trp Gln Gln Gly Gln Lys Leu Tyr Leu Pro Pro Thr Pro
 1               5                  10                  15

Val Ser Lys Val Leu Cys Ser Glu Thr Tyr Val Gln Arg Lys Ser Ile
             20                  25                  30

Phe Tyr His Ala Glu Thr Glu Arg Leu Leu Thr Ile Gly His Pro Tyr
         35                  40                  45

Tyr Pro Val Ser Ile Gly Ala Lys Thr Val Pro Lys Val Ser Ala Asn
     50                  55                  60

Gln Tyr Arg Val Phe Lys Ile Gln Leu Pro Asp Pro Asn Gln Phe Ala
 65                  70                  75                  80

Leu Pro Asp Arg Thr Val His Asn Pro Ser Lys Glu Arg Leu Val Trp
                 85                  90                  95

Pro Val Ile Gly Val Gln Val Ser Arg Gly Gln Pro Leu Gly Gly Thr
            100                 105                 110

Val Thr Gly His Pro Thr Phe Asn Ala Leu Leu Asp Ala Glu Asn Val
        115                 120                 125

Asn Arg Lys Val Thr Thr Gln Thr Thr Asp Asp Arg Lys Gln Thr Gly
130                 135                 140

Leu Asp Ala Lys Gln Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asn Phe Lys Glu
        195                 200                 205

Ile Asn Ala Ser Lys Ser Asp Leu Pro Leu Asp Ile Gln Asn Glu Ile
210                 215                 220

Cys Leu Tyr Pro Asp Tyr Leu Lys Met Ala Glu Asp Ala Ala Gly Asn
225                 230                 235                 240

Ser Met Phe Phe Phe Ala Arg Lys Glu Gln Val Tyr Val Arg His Ile
                245                 250                 255

Trp Thr Arg Gly Gly Ser Glu Lys Glu Ala Pro Thr Thr Asp Phe Tyr
            260                 265                 270

Leu Lys Asn Asn Lys Gly Asp Ala Thr Leu Lys Ile Pro Ser Val His
        275                 280                 285

Phe Gly Ser Pro Ser Gly Ser Leu Val Ser Thr Asp Asn Gln Ile Phe
    290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
                325                 330                 335

Thr Asn Leu Thr Ile Ser Val Ala Ser Asp Gly Thr Pro Leu Thr Glu
            340                 345                 350

Tyr Asp Ser Ser Lys Phe Asn Val Tyr His Arg His Met Glu Glu Tyr
```

-continued

```
            355                 360                 365
Lys Leu Ala Phe Ile Leu Glu Leu Cys Ser Val Glu Ile Thr Ala Gln
            370                 375                 380
Thr Val Ser His Leu Gln Gly Leu Met Pro Ser Val Leu Glu Asn Trp
385                 390                 395                 400
Glu Ile Gly Val Gln Pro Pro Thr Ser Ser Ile Leu Glu Asp Thr Tyr
                405                 410                 415
Arg Tyr Ile Glu Ser Pro Ala Thr Lys Cys Ala Ser Asn Val Ile Pro
                420                 425                 430
Ala Lys Glu Asp Pro Tyr Ala Gly Phe Lys Phe Trp Asn Ile Asp Leu
            435                 440                 445
Lys Glu Lys Leu Ser Leu Asp Leu Asp Gln Phe Pro Leu Gly Arg Arg
    450                 455                 460
Phe Leu Ala Gln Gln Asp Ile Asp
465                 470
```

<210> SEQ ID NO 2
<211> LENGTH: 1416
<212> TYPE: DNA
<213> ORGANISM: Bovine papilloma virus

<400> SEQUENCE: 2

| | | | | | |
|---|---|---|---|---|---|
| atggcgttgt | ggcaacaagg | ccagaagctg | tatctccctc | caccccctgt | aagcaaggtg | 60 |
| ctttgcagtg | aaacctatgt | gcaaagaaaa | agcattttt | atcatgcaga | aacggagcgc | 120 |
| ctgctaacta | taggacatcc | atattaccca | gtgtctatcg | ggccaaaac | tgttcctaag | 180 |
| gtctctgcaa | atcagtatag | ggtatttaaa | atacaactac | ctgatcccaa | tcaatttgca | 240 |
| ctacctgaca | ggactgttca | aacccaagt | aaagagcggc | tggtgtggcc | agtcataggt | 300 |
| gtgcaggtgt | ccagagggca | gcctcttgga | ggtactgtaa | ctgggcaccc | cacttttaat | 360 |
| gctttgcttg | atgcagaaaa | tgtgaataga | aaagtcacca | cccaaacaac | agatgacagg | 420 |
| aaacaaacag | gcctagatgc | taagcaacaa | cagattctgt | tgctaggctg | taccctgct | 480 |
| gaaggggaat | attggacaac | agcccgtcca | tgtgttactg | atcgtctaga | aaatggcgcc | 540 |
| tgccctcctc | ttgaattaaa | aaacaagcac | atagaagatg | gggatatgat | ggaaattggg | 600 |
| tttggtgcag | ccaacttcaa | agaaattaat | gcaagtaaat | cagatctacc | tcttgacatt | 660 |
| caaaatgaga | tctgcttgta | cccagactac | ctcaaaatgg | ctgaggacgc | tgctggtaat | 720 |
| agcatgttct | tttttgcaag | gaagaacag | gtgtatgtta | gacacatctg | gaccagaggg | 780 |
| ggctcggaga | agaagcccc | taccacagat | ttttatttaa | agaataataa | agggatgcc | 840 |
| acccttaaaa | tacccagtgt | gcattttggt | agtcccagtg | gctcactagt | ctcaactgat | 900 |
| aatcaaattt | ttaatcggcc | ctactggcta | ttccgtgccc | agggcatgaa | caatggaatt | 960 |
| gcatggaata | atttattgtt | tttaacagtg | ggggacaata | cacgtggtac | taatcttacc | 1020 |
| ataagtgtag | cctcagatgg | aacccccacta | acagagtatg | atagctcaaa | attcaatgta | 1080 |
| taccatagac | atatggaaga | atataagcta | gcctttatat | tagagctatg | ctctgtggaa | 1140 |
| atcacagctc | aaactgtgtc | acatctgcaa | ggacttatgc | cctctgtgct | tgaaaattgg | 1200 |
| gaaataggtg | tgcagcctcc | tacctcatcg | atattagagg | acacctatcg | ctatatagag | 1260 |
| tctcctgcaa | ctaaatgtgc | aagcaatgta | attcctgcaa | agaagaccc | ttatgcaggg | 1320 |
| tttaagttt | ggaacataga | tcttaaagaa | aagctttctt | tggacttaga | tcaatttccc | 1380 |
| ttgggaagaa | gatttttagc | acagcaatat | cgatat | | | 1416 |

<210> SEQ ID NO 3
<211> LENGTH: 137
<212> TYPE: PRT
<213> ORGANISM: Bovine papilloma virus

<400> SEQUENCE: 3

```
Met Asp Leu Lys Pro Phe Ala Arg Thr Asn Pro Phe Ser Gly Leu Asp
 1               5                  10                  15

Cys Leu Trp Cys Arg Glu Pro Leu Thr Glu Val Asp Ala Phe Arg Cys
             20                  25                  30

Met Val Lys Asp Phe His Val Val Ile Arg Glu Gly Cys Arg Tyr Gly
         35                  40                  45

Ala Cys Thr Ile Cys Leu Glu Asn Cys Leu Ala Thr Glu Arg Arg Leu
     50                  55                  60

Trp Gln Gly Val Pro Val Thr Gly Glu Glu Ala Glu Leu Leu His Gly
 65                  70                  75                  80

Lys Thr Leu Asp Arg Leu Cys Ile Arg Cys Tyr Cys Gly Gly Lys
                 85                  90                  95

Leu Thr Lys Asn Glu Lys His Arg His Val Leu Phe Asn Glu Pro Phe
                100                 105                 110

Cys Lys Thr Arg Ala Asn Ile Ile Arg Gly Arg Cys Tyr Asp Cys Cys
            115                 120                 125

Arg His Gly Ser Arg Ser Lys Tyr Pro
        130                 135
```

<210> SEQ ID NO 4
<211> LENGTH: 414
<212> TYPE: DNA
<213> ORGANISM: Bovine papilloma virus

<400> SEQUENCE: 4

```
atggacctga aacctttgc aagaaccaat ccattctcag ggttggattg tctgtggtgc      60
agagagcctc ttacagaagt tgatgctttt aggtgcatgg tcaaagactt tcatgttgta    120
attcgggaag ctgtagata tggtgcatgt accatttgtc ttgaaaactg tttagctact    180
gaaagaagac tttggcaagg tgttccagta acaggtgagg aagctgaatt attgcatggc    240
aaaacacttg ataggctttg cataagatgc tgctactgtg ggggcaaact aacaaaaaat    300
gaaaaacatc ggcatgtgct ttttaatgag cctttctgca aaaccagagc taacataatt    360
agaggacgct gctacgactg ctgcagacat ggttcaaggt ccaaataccc atag          414
```

<210> SEQ ID NO 5
<211> LENGTH: 126
<212> TYPE: PRT
<213> ORGANISM: Bovine papilloma virus

<400> SEQUENCE: 5

```
Met Val Gln Gly Pro Asn Thr His Arg Asn Leu Asp Asp Ser Pro Ala
 1               5                  10                  15

Gly Pro Leu Leu Ile Leu Ser Pro Cys Ala Gly Thr Pro Thr Arg Ser
             20                  25                  30

Pro Ala Ala Asp Ala Pro Asp Phe Arg Leu Pro Cys His Phe Gly Arg
         35                  40                  45

Pro Thr Arg Lys Arg Gly Pro Thr Thr Pro Leu Ser Ser Pro Gly
     50                  55                  60

Lys Leu Cys Ala Thr Gly Pro Arg Arg Val Tyr Ser Val Thr Val Cys
 65                  70                  75                  80
```

-continued

```
Cys Gly Asn Cys Gly Lys Glu Leu Thr Phe Ala Val Lys Thr Ser Ser
                 85                  90                  95

Thr Ser Leu Leu Gly Phe Glu His Leu Leu Asn Ser Asp Leu Asp Leu
            100                 105                 110

Leu Cys Pro Arg Cys Glu Ser Arg Glu Arg His Gly Lys Arg
        115                 120                 125

<210> SEQ ID NO 6
<211> LENGTH: 384
<212> TYPE: DNA
<213> ORGANISM: Bovine papilloma virus

<400> SEQUENCE: 6
atggttcaag gtccaaatac ccatagaaac ttggatgatt cacctgcagg accgttgctg      60
attttaagtc catgtgcagg cacacctacc aggtctcctg cagcacctga tgcacctgat     120
ttcagacttc cgtgccattt cggccgtcct actaggaagc gaggtcccac tacccctccg     180
ctttcctctc ccggaaaact gtgtgcaaca gggccacgtc gagtgtattc tgtgactgtc     240
tgctgtggaa actgcggaaa agagctgact tttgctgtga agaccagctc gacgtccctg     300
cttggatttg aacaccttt aaactcagat ttagacctct tgtgtccacg ttgtgaatct     360
cgcgagcgtc atggcaaacg ataa                                          384

<210> SEQ ID NO 7
<211> LENGTH: 137
<212> TYPE: PRT
<213> ORGANISM: Bovine papilloma virus

<400> SEQUENCE: 7

Met Asp Leu Lys Pro Phe Ala Arg Thr Asn Pro Phe Ser Gly Leu Asp
 1               5                  10                  15

Cys Leu Trp Cys Arg Glu Pro Leu Thr Glu Val Asp Ala Phe Arg Cys
            20                  25                  30

Met Val Lys Asp Phe His Val Val Ile Arg Glu Gly Cys Arg Tyr Gly
        35                  40                  45

Ala Cys Thr Ile Cys Leu Glu Asn Cys Leu Ala Thr Glu Arg Arg Leu
    50                  55                  60

Trp Gln Gly Val Pro Val Thr Gly Glu Glu Ala Glu Leu Leu His Gly
65                  70                  75                  80

Lys Thr Leu Asp Arg Leu Cys Ile Arg Cys Cys Tyr Cys Gly Gly Lys
                85                  90                  95

Leu Thr Lys Asn Glu Lys His Arg His Val Leu Phe Asn Glu Pro Phe
            100                 105                 110

Cys Lys Thr Arg Ala Asn Ile Ile Arg Gly Arg Cys Tyr Asp Cys Cys
        115                 120                 125

Arg His Gly Ser Arg Ser Lys Tyr Pro
    130                 135

<210> SEQ ID NO 8
<211> LENGTH: 414
<212> TYPE: DNA
<213> ORGANISM: Bovine papilloma virus

<400> SEQUENCE: 8
atggacctgc aaagtttttc cagaggcaat cctttctcag gattggcctg tgtttggtgc      60
agggagcctc tcacagaagt tgatgctttt aggtgcatga taaagacttt tcatgttgta     120
```

-continued

```
taccgagatg gtgtgaaatt tggtgcatgt accacttgtc ttgagaactg cttagataaa      180
gaaagaagac tgtggaaagg tgtgccagta acaggtgagg aagctcaatt attgcatggc      240
aaatcccttg ataggctttg cataagatgc tgctactgtg ggggaaaact aaccaaaaac      300
gagaagcagc ggcatgtgct ttataatgag ccttttttgca aaacgagatc taacataata    360
agaggacgct gctacgactg ctgcagacat ggttcaaggt ccaactaccc atag           414
```

<210> SEQ ID NO 9
<211> LENGTH: 127
<212> TYPE: PRT
<213> ORGANISM: Bovine papilloma virus

<400> SEQUENCE: 9

```
Met Val Gln Gly Pro Thr Thr His Arg Asn Leu Asp Asp Ser Pro Ala
  1               5                  10                  15

Gly Pro Leu Leu Ile Leu Ser Pro Cys Ala Gly Thr Pro Thr Arg Val
             20                  25                  30

Pro Ala Ala Pro Cys Ala Pro Asp Phe Arg Leu Pro Cys His Phe Gly
         35                  40                  45

Arg Pro Thr Arg Lys Arg Gly Pro Ser Thr Pro Leu Ser Ser Pro
     50                  55                  60

Gly Lys Val Cys Ala Thr Gly Pro Arg Arg Val Tyr Ser Val Thr Val
 65                  70                  75                  80

Cys Cys Gly His Cys Gly Lys Asp Leu Thr Phe Ala Val Lys Thr Gly
                 85                  90                  95

Ser Thr Thr Leu Leu Gly Phe Glu His Leu Leu Asn Ser Asp Leu Asp
            100                 105                 110

Leu Leu Cys Pro Arg Cys Glu Ser Arg Glu Arg His Gly Lys Arg
            115                 120                 125
```

<210> SEQ ID NO 10
<211> LENGTH: 384
<212> TYPE: DNA
<213> ORGANISM: Bovine papilloma virus

<400> SEQUENCE: 10

```
atggttcaag gtccaactac ccatagaaac ttggatgatt cacctgcagg accgttgctg      60
attttaagtc catgtgcagg cacacctacc agggttcctg cagcacctga tgcacccgat     120
ttcagacttc cgtgccattt cggccgtcct actaggaagc gaggtccctc tacgcctccg     180 cttcctctc ccggaaaagt gtgtgcaaca gggccacgtc gagtgtactc tgtgactgtc      240
tgctgcggac actgcggaaa ggaccttaca tttgctgtca agactggctc tacgaccttg     300
ctgggcttcg aacaccctatt aaactcagat ttggacctgt tgtgtccccg ttgcgaatct    360
cgcgagcgtc atggcaaacg ataa                                            384
```

<210> SEQ ID NO 11
<211> LENGTH: 472
<212> TYPE: PRT
<213> ORGANISM: Bovine papilloma virus

<400> SEQUENCE: 11

```
Met Ala Leu Trp Gln Gln Gly Gln Lys Leu Tyr Leu Pro Pro Thr Pro
  1               5                  10                  15

Val Ser Lys Val Leu Cys Ser Glu Thr Tyr Val Gln Arg Lys Ser Ile
             20                  25                  30

Phe Tyr His Ala Glu Thr Glu Arg Leu Leu Thr Val Gly His Pro Tyr
```

```
                35                  40                  45
Tyr Gln Val Thr Val Gly Asp Lys Thr Val Pro Lys Val Ser Ala Asn
             50                  55                  60

Gln Phe Arg Val Phe Lys Ile Gln Leu Pro Asp Pro Asn Gln Phe Ala
 65                  70                  75                  80

Leu Pro Asp Arg Thr Val His Asn Pro Ser Lys Glu Arg Leu Val Trp
                 85                  90                  95

Ala Val Ile Gly Val Gln Val Ser Arg Gly Gln Pro Leu Gly Gly Thr
            100                 105                 110

Val Thr Gly His Pro Thr Glu Asn Ala Leu Leu Asp Ala Glu Asn Val
            115                 120                 125

Asn Arg Lys Val Thr Ala Gln Thr Thr Asp Asp Arg Lys Gln Thr Gly
130                 135                 140

Leu Asp Ala Lys Gln Gln Ile Leu Leu Leu Gly Cys Thr Pro Ala
145                 150                 155                 160

Glu Gly Glu Tyr Trp Thr Thr Ala Arg Pro Cys Val Thr Asp Arg Leu
                165                 170                 175

Glu Asn Gly Ala Cys Pro Pro Leu Glu Leu Lys Asn Lys His Ile Glu
            180                 185                 190

Asp Gly Asp Met Met Glu Ile Gly Phe Gly Ala Ala Asp Phe Lys Thr
            195                 200                 205

Leu Asn Ala Ser Lys Ser Asp Leu Pro Leu Asp Ile Gln Asn Glu Ile
            210                 215                 220

Cys Leu Tyr Pro Asp Tyr Leu Lys Met Ala Glu Asp Ala Ala Gly Asn
225                 230                 235                 240

Ser Met Phe Phe Phe Ala Arg Lys Glu Gln Val Tyr Val Arg His Ile
                245                 250                 255

Trp Thr Arg Gly Gly Ser Glu Lys Glu Ala Pro Ser Lys Asp Phe Tyr
                260                 265                 270

Leu Lys Asn Gly Arg Gly Glu Glu Thr Leu Lys Ile Pro Ser Val His
            275                 280                 285

Phe Gly Ser Pro Ser Gly Ser Leu Val Ser Thr Asp Asn Gln Ile Phe
290                 295                 300

Asn Arg Pro Tyr Trp Leu Phe Arg Ala Gln Gly Met Asn Asn Gly Ile
305                 310                 315                 320

Ala Trp Asn Asn Leu Leu Phe Leu Thr Val Gly Asp Asn Thr Arg Gly
                325                 330                 335

Thr Asn Leu Ser Ile Ser Val Ala Ala Asp Gly Asn Ala Leu Ser Glu
            340                 345                 350

Tyr Asp Thr Gly Lys Phe Asn Leu Tyr His Arg His Met Glu Glu Tyr
            355                 360                 365

Lys Leu Ala Phe Ile Leu Glu Leu Cys Ser Val Glu Ile Thr Ala Gln
            370                 375                 380

Thr Leu Ser His Leu Gln Gly Leu Met Pro Ser Val Leu Gln Asn Trp
385                 390                 395                 400

Glu Ile Gly Val Gln Pro Pro Ala Ser Ser Ile Leu Glu Asp Thr Tyr
                405                 410                 415

Arg Tyr Glu Glu Ser Pro Ala Thr Lys Cys Ala Ser Asn Val Ile Pro
            420                 425                 430

Pro Lys Glu Asp Pro Tyr Ala Gly Leu Lys Phe Trp Ser Ile Asp Leu
            435                 440                 445

Lys Glu Lys Leu Ser Leu Asp Leu Asp Gln Phe Pro Leu Gly Arg Arg
450                 455                 460
```

Phe Leu Ala Gln Gln Gly Ala Gly
465             470

<210> SEQ ID NO 12
<211> LENGTH: 1416
<212> TYPE: DNA
<213> ORGANISM: Bovine papilloma virus

<400> SEQUENCE: 12

| | | | | | |
|---|---|---|---|---|---:|
| atggcgttgt | ggcaacaagg | ccaaaagctg | tatctccctc | caacccctgt | aagcaaggtg | 60 |
| ctatgcagtg | aaacctatgt | gcaaagaaaa | agcatattct | atcatgcaga | aacggaacgc | 120 |
| ctgttaactg | taggacatcc | atactaccaa | gtcactgtgg | gggacaaaac | tgttcccaaa | 180 |
| gtgtctgcta | atcaatttag | agttttttaaa | atacagctcc | ccgatcccaa | tcagtttgca | 240 |
| ttgcctgata | ggactgtgca | caatccaagc | aaggagcgcc | tggtttgggc | tgtaataggg | 300 |
| gttcaagtat | ctcgtggcca | accactagga | ggcacagtta | ctgggcaccc | cacttttaat | 360 |
| gctctgcttg | atgcagaaaa | tgttaataga | aagttactg | cacaaacaac | agatgacagg | 420 |
| aagcaaacag | gattagatgc | taagcaacaa | cagattctgt | tgctgggctg | tacccctgca | 480 |
| gaagggaat | actggaccac | agcccgtcca | tgtgttactg | atagactaga | aatggtgcg | 540 |
| tgtcctcctt | tagaattaaa | gaacaaacac | atagaagatg | gagacatgat | ggaaataggg | 600 |
| tttggtgctg | ctgactttaa | aacactaaat | gccagtaaat | cagatctacc | tcttgacatt | 660 |
| caaaatgaaa | tatgcctgta | tccagactac | ctcaaaatgg | ctgaagatgc | tgctggaaac | 720 |
| agtatgttct | tctttgcaag | aaaagaacaa | gtgtatgtaa | ggcatatatg | gactcggggg | 780 |
| ggctctgaaa | agaagcacc | cagtaaagac | ttctacctca | aaaatggtag | aggtgaagaa | 840 |
| actctaaaaa | tacctagtgt | gcactttggc | agtcccagtg | gatccttggt | gtccactgat | 900 |
| aatcaaatat | taacaggcc | ttattggcta | ttcagggctc | agggcatgaa | caatgggatt | 960 |
| gcatggaata | atttattatt | tttaactgta | ggggataaca | cacggggaac | taaccttagt | 1020 |
| attagtgtag | ctgcagatgg | aaacgcattg | tcagagtatg | atactggcaa | atttaaccta | 1080 |
| taccataggc | atatggaaga | atataagcta | gcatttatat | tggagctgtg | ctctgttgag | 1140 |
| attactgcac | aaacactgtc | acatgtgcaa | ggactgatgc | cctctgtgct | acaaaactgg | 1200 |
| gaaatcgggg | tgcaacctcc | tgcttcttct | attttagaag | atacttatag | gtacatagag | 1260 |
| tctcctgcaa | ctaaatgtgc | aagtaatgtt | ataccaccca | agaagaccc | ttatgcaggg | 1320 |
| cttaagttttt | ggagcataga | cttaaaagaa | aagctgtctt | tggacttaga | ccaatttccc | 1380 |
| ttgggaagaa | gattcttagc | tcagcaatat | cgatat | | | 1416 |

<210> SEQ ID NO 13
<211> LENGTH: 137
<212> TYPE: PRT
<213> ORGANISM: Bovine papilloma virus

<400> SEQUENCE: 13

Met Asp Leu Lys Pro Phe Ala Arg Thr Asn Pro Phe Ser Gly Leu Asp
 1               5                  10                  15

Cys Leu Trp Cys Arg Glu Pro Leu Thr Glu Val Asp Ala Phe Arg Cys
            20                  25                  30

Met Val Lys Asp Phe His Val Val Ile Arg Glu Gly Cys Arg Tyr Gly
        35                  40                  45

Ala Cys Thr Ile Cys Leu Glu Asn Cys Leu Ala Thr Glu Arg Arg Leu
    50                  55                  60

```
Trp Gln Gly Val Pro Val Thr Gly Glu Glu Ala Glu Leu Leu His Gly
 65                  70                  75                  80

Lys Thr Leu Asp Arg Leu Cys Ile Arg Cys Cys Tyr Cys Gly Gly Lys
             85                  90                  95

Leu Thr Lys Asn Glu Lys His Arg His Val Leu Phe Asn Glu Pro Phe
            100                 105                 110

Cys Lys Thr Arg Ala Asn Ile Ile Arg Gly Arg Cys Tyr Asp Cys Cys
            115                 120                 125

Arg His Gly Ser Arg Ser Lys Tyr Pro
            130                 135
```

```
<210> SEQ ID NO 14
<211> LENGTH: 414
<212> TYPE: DNA
<213> ORGANISM: Bovine papilloma virus

<400> SEQUENCE: 14
atggacctga aacctttgc aagaaccaat ccattctcag ggttggattg tctgtggtgc    60
agagagcctc ttacagaagt tgatgctttt aggtgcatgg tcaaagactt tcatgttgta   120
attcgggaag gctgtagata tggtgcatgt accatttgtc ttgaaaactg tttagctact   180
gaaagaagac tttggcaagg tgttccagta acaggtgagg aagctgaatt attgcatggc   240
aaaaacacttg ataggctttg cataagatgc tgctactgtg ggggcaaact aacaaaaaat   300
gaaaaacatc ggcatgtgct ttttaatgag cctttctgca aaaccagagc taacataatt   360
agaggacgct gctacgactg ctgcagacat ggttcaaggt ccaaataccc atag         414
```

```
<210> SEQ ID NO 15
<211> LENGTH: 127
<212> TYPE: PRT
<213> ORGANISM: Bovine papilloma virus

<400> SEQUENCE: 15

Met Val Gln Gly Pro Asn Thr His Arg Asn Leu Asp Asp Ser Pro Ala
  1               5                  10                  15

Gly Pro Leu Leu Ile Leu Ser Pro Cys Ala Gly Thr Pro Thr Arg Ser
             20                  25                  30

Pro Ala Ala Pro Asp Ala Pro Asp Phe Arg Leu Pro Cys His Phe Gly
         35                  40                  45

Arg Pro Thr Arg Lys Arg Gly Pro Thr Thr Pro Pro Leu Ser Ser Pro
     50                  55                  60

Gly Lys Leu Cys Ala Thr Gly Pro Arg Arg Val Tyr Ser Val Thr Val
 65                  70                  75                  80

Cys Cys Gly Asn Cys Gly Lys Glu Leu Thr Phe Ala Val Lys Thr Ser
             85                  90                  95

Ser Thr Ser Leu Leu Gly Phe Glu His Leu Leu Asn Ser Asp Leu Asp
            100                 105                 110

Leu Leu Cys Pro Arg Cys Glu Ser Arg Glu Arg His Gly Lys Arg
            115                 120                 125
```

```
<210> SEQ ID NO 16
<211> LENGTH: 384
<212> TYPE: DNA
<213> ORGANISM: Bovine papilloma virus

<400> SEQUENCE: 16
atggttcaag gtccaaatac ccatagaaac ttggatgatt cacctgcagg accgttgctg    60
```

```
attttaagtc catgtgcagg cacacctacc aggtctcctg cagcacctga tgcacctgat      120
ttcagacttc cgtgccattt cggccgtcct actaggaagc gaggtcccac taccectccg      180 ctttcctctc ccggaaaact gtgtgcaaca gggccacgtc gagtgtattc tgtgactgtc      240
tgctgtggaa actgcggaaa agagctgact tttgctgtga agaccagctc gacgtccctg      300
cttggatttg aacaccttt aaactcagat ttagacctct tgtgtccacg ttgtgaatct      360
cgcgagcgtc atggcaaacg ataa                                             384
```

<210> SEQ ID NO 17
<211> LENGTH: 137
<212> TYPE: PRT
<213> ORGANISM: Bovine papilloma virus

<400> SEQUENCE: 17

```
Met Asp Leu Gln Ser Phe Ser Arg Gly Asn Pro Phe Ser Gly Leu Ala
 1               5                  10                  15

Cys Val Trp Cys Arg Glu Pro Leu Thr Glu Val Asp Ala Phe Arg Cys
                20                  25                  30

Met Ile Lys Asp Phe His Val Val Tyr Arg Asp Gly Val Lys Phe Gly
            35                  40                  45

Ala Cys Thr Thr Cys Leu Glu Asn Cys Leu Asp Lys Glu Arg Arg Leu
    50                  55                  60

Trp Lys Gly Val Pro Val Thr Gly Glu Glu Ala Gln Leu Leu His Gly
65                  70                  75                  80

Lys Ser Leu Asp Arg Leu Cys Ile Arg Cys Tyr Cys Gly Gly Lys
                85                  90                  95

Leu Thr Lys Asn Glu Lys Gln Arg His Val Leu Tyr Asn Glu Pro Phe
            100                 105                 110

Cys Lys Thr Arg Ser Asn Ile Ile Arg Gly Arg Cys Tyr Asp Cys Cys
        115                 120                 125

Arg His Gly Ser Arg Ser Asn Tyr Pro
    130                 135
```

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH:
<212> TYPE:
<213> ORGANISM:

<400> SEQUENCE: 20

000

```
<210> SEQ ID NO 21
<220> FEATURE:
<221> NAME/KEY: primer_bind
<222> LOCATION: (1)...(39)
<211> LENGTH:
<212> TYPE:
<213> ORGANISM:

<400> SEQUENCE: 21

000

<210> SEQ ID NO 22
<220> FEATURE:
<221> NAME/KEY: primer_bind
<222> LOCATION: (1)...(41)
<211> LENGTH:
<212> TYPE:
<213> ORGANISM:

<400> SEQUENCE: 22

000

<210> SEQ ID NO 23
<220> FEATURE:
<221> NAME/KEY: primer_bind
<222> LOCATION: (0)...(0)
<211> LENGTH:
<212> TYPE:
<213> ORGANISM:

<400> SEQUENCE: 23

000

<210> SEQ ID NO 24
<220> FEATURE:
<221> NAME/KEY: primer_bind
<222> LOCATION: (1)...(40)
<211> LENGTH:
<212> TYPE:
<213> ORGANISM:

<400> SEQUENCE: 24

000

<210> SEQ ID NO 25
<220> FEATURE:
<221> NAME/KEY: primer_bind
<222> LOCATION: (1)...(44)
<211> LENGTH:
<212> TYPE:
<213> ORGANISM:

<400> SEQUENCE: 25

000
```